United States Patent [19]

Mathieu

[11] Patent Number: 5,616,305
[45] Date of Patent: Apr. 1, 1997

[54] FLEXIBLE MEDICAL HEMODIALYSIS PACKAGING UNIT FOR THE PRODUCTION OF CONCENTRATED DIALYSIS SOLUTION INCLUDING A DEVICE FOR THE SAME

[75] Inventor: Bernd Mathieu, Spiesen, Germany

[73] Assignee: Fresenius AG, Bad Homburg v.d.H., Germany

[21] Appl. No.: 490,217

[22] Filed: Jun. 14, 1995

[30] Foreign Application Priority Data

Jun. 24, 1994 [DE] Germany ............... 44 22 100.2

[51] Int. Cl.$^6$ .................................................. B01D 11/02
[52] U.S. Cl. ............... 422/261; 206/568; 206/570; 422/267; 422/279; 422/283
[58] Field of Search .................... 422/261, 266, 422/267, 279, 282, 283; 604/408–410; 206/568, 570, 484, 524.1, 526, 828

[56] References Cited

U.S. PATENT DOCUMENTS

| | | | |
|---|---|---|---|
| 2,771,346 | 11/1956 | Lambers | 422/282 X |
| 4,368,729 | 1/1983 | Dossin | 728/214 D |
| 4,386,634 | 6/1983 | Stasz et al. | 141/2 |
| 4,664,891 | 5/1987 | Consentino et al. | 422/269 |
| 4,994,057 | 2/1991 | Carmen et al. | 604/416 |
| 5,344,392 | 9/1994 | Senninger et al. | 604/4 |
| 5,385,564 | 1/1995 | Slater et al. | 604/416 |

FOREIGN PATENT DOCUMENTS

| | | |
|---|---|---|
| 3212230A1 | 3/1982 | Germany. |
| 4139165A1 | 11/1991 | Germany. |
| PCT/SE93/00191 | 3/1993 | Sweden. |

*Primary Examiner*—Robert J. Warden
*Assistant Examiner*—Krisanne M. Thornton
*Attorney, Agent, or Firm*—Robbins, Berliner & Carson, LLP

[57] ABSTRACT

A flexible medical packaging unit designed as a bag (14) including a single connector (18) containing a powdered salt concentrate (16), i.e. bicarbonate, with a volume sufficient for one dialysis treatment. The bag (14) has such a capacity that the powdered salt concentrate (16) will only partially be dissolved even when completely filled with water.

17 Claims, 3 Drawing Sheets

FLEXIBLE MEDICAL HEMODIALYSIS PACKAGING UNIT FOR THE PRODUCTION OF CONCENTRATED DIALYSIS SOLUTION INCLUDING A DEVICE FOR THE SAME

DESCRIPTION

The invention refers to a flexible medical hemodialysis packaging unit for the production of a concentrated dialysis solution including a bag having one single connector and a cavity filled with a powdered salt concentrate of a volume adequate for one dialysis treatment.

Hemodialysis solution must be produced for hemodialysis based on an electrolyte content essentially corresponding to that of the blood of a patient to be treated.

Processes have been known for some time in which ready-to-use hemodialysis solution is produced in a single stage from ready-to-use liquid concentrates supplied in containers. Furthermore, processes are known by which hemodialysis solution is produced in a tank at the bedside (also single-stage) by using a dry concentrate and water.

On the other hand, however, a liquid concentrate may be produced from a dry concentrate by mixing with water, based on a two-stage method, with the required hemodialysis solution being subsequently produced by further mixing with water in a predetermined ratio.

A process of the latter type is described in DE 32 12 230, in which initially a dry concentrate is provided in a mixing chamber connected at its inlet side to a water supply and at its outlet side to a hemodialysis solution tank. This allows production of an individually adapted liquid concentrate and from this a ready-to-use hemodialysis solution. This mixing chamber essentially has the task not only to transfer to the outlet line any electrolytic salts which are easily soluble, such as sodium chloride, potassium chloride or calcium chloride, but also sodium bicarbonate, which is not so easily soluble in water, in a dissolved form. As this is generally the case in batch processes, the product is mixed volumetrically, i.e. by a predetermined quantity of dry concentrate being mixed with a predetermined volume of water. Based on this mixing principle, the liquid concentrate is prepared from a dry concentrate and water in a first container, at least partially continuously, and in another option a ready-to-use hemodialysis solution is prepared from a liquid and water in the same or another container, with this container containing a full volume of hemodialysis solution for one treatment.

DE 34 43 911 describes a process in which a liquid concentrate is prepared from dry concentrate and water in a mixing container having an inlet and outlet line. On the outlet side the liquid concentrate may be passed to a mixing point to which a predetermined volume of water is supplied by a second line. Generally, a liquid concentrate batch for one treatment is produced in the mixing container, subsequently allowing that one complete hemodialysis solution batch is produced by continuous mixing of a liquid concentrate with water.

Another process is described in U.S. Pat. No. 4,386,634 in which a hemodialysis solution may be produced from dry concentrate by means of a two-stage process as this is also the subject matter of the invention. In this case, a bag is used as a mixing container for the production of a liquid concentrate in batches which is continuously discharged during treatment to a mixing point which is also supplied by water under pressure for the production of a ready-to-use hemodialysis solution. Although production of a liquid concentrate offers the advantage of safe mixing of a dry concentrate with water, it also suffers of the shortcoming that a relatively large space is required for the concentrate (8–12 l), therefore necessitating stable containers or expensive storage and retention devices. Both arrangements are therefore associated with relatively high costs for disinfecting and/or making them available.

In so far it was endeavoured (EP 278 100) to produce dialysis solutions by providing a solid concentrate of a relatively low volume in a cartridge having a water inlet and a liquid concentrate outlet. This cartridge is charged with a mono-substance, usually sodium bicarbonate, supplied with pressurised water from the cartridge inlet side, with the bicarbonate slowly dissolving whilst the liquid is flowing through the cartridge, forming a liquid concentrate. This concentrate is passed to a mixing point through the outlet where it is diluted with water and other liquid concentrates to obtain a dialysis solution of a predetermined composition.

This continuous process has the advantage of low space requirements for the concentrate and a good storage life of the dry concentrate in the cartridge in comparison to a liquid concentrate supplied in a container. The disadvantage of this process and its arrangement is the fact that the powder must be continuously flushed with water in order to obtain the required saturation of the solution by dissolving the salt. It is a known fact that approx. 100 g of sodium bicarbonate are dissolved in 1 l of water at ambient temperature. This saturation must be ensured at the outlet of the cartridge, which, however, often cannot be ensured due to frequent clogging of the powder and the risk of channel effects within the cartridge by continuous flushing with water. In this respect problems occur in the production of a ready-to-use hemodialysis solution, especially prevalent when the mixing ratio of water and an equal volume of concentrate is high.

Furthermore, the connectors of the two ports are prone to well-known hygiene and confusion problems.

Another means for the continuous production of a liquid concentrate is described in DE 41 39 165 in which, however, no channelling, hygiene and confusion problems, as referred to above, can occur.

The invention is therefore based on the task of making available a packaging unit and a device for the production of a liquid hemodialysis solution allowing the continuous production at the bedside of a saturated, liquid concentrate not prone to channelling and storage problems.

This problem is solved on the one hand by making available a flexible medical packaging unit only including one single connector, thus reducing sterility problems to a minimum. In the same way, the contents of the packaging unit is such that saturated hemodialysis concentrates can be produced in batches, i.e. during treatment of a patient the packaging unit will have to be replenished several times with fresh water in order to produce batches of liquid concentrates (multi-batch process).

From the device point of view, this task is solved by making available a device for the production of a liquid hemodialysis concentrate including a water supply, a flexible container with one single connector, holding sufficient powder concentrate for one dialysis treatment, a hose system, connecting the water supply on the one hand and the connector and the device for the production of a hemodialysis solution on the other, a closing device, individually opening and/or closing a water supply, a connector and a dialysis solution device and a device for compensating the dead volume of the hose system.

In this arrangement, a relatively small single concentrate volume is produced in relation to the total hemodialysis solution required, which is diluted in batches to obtain a ready-made hemodialysis solution.

According to a first embodiment, the shut-off device includes valves arranged in the hose system as follows. A first valve is provided in a first hose section, connecting the water supply to a connecting point, with a second hose section connected to the connector of the flexible container. A second valve is arranged in this second hose section. Furthermore, a third hose section is branched from the connecting point, including a third valve which is connected at its end to a device to produce a ready-to-use hemodialysis solution.

These valves 1–3 are activated according to a predetermined mixing process, i.e. they are opened, followed by de-activating, i.e. closing.

The water supply which usually makes available reverse osmosis water (RO water) is usually pressurised. Therefore in general no pumping device is required for supplying the water. On the other hand, however, a pump system may be included in the hose system for supplying a flexible container with fresh water and removing the mixed solution concentrate from the container. If required, removal may also be by a pump included in the system to produce a ready-to-use dialysis solution.

According to a first embodiment, the hose system within the area of the connecting point usually includes a metering pump through a fourth hose section which includes a volumetric pump. This pump will act both as an inlet and outlet pump. Its capacity is usually smaller than the capacity of the flexible container. Therefore several pumping cycles will be needed in order to fill its cavity with a predetermined volume of water.

In order to trigger the pump charging cycle, initially the first valve is opened whilst the two other valves are closed. The pump, which is then filled with water, is discharged into the flexible container in one step, whilst the second valve is open and the first and third valves are closed. This cycle is repeated several times until a predetermined volume of water has been transferred to the flexible container, preferably designed as a bag.

Due to the flexible container only having one connector, it also includes a common hose section for the water supply and the liquid concentrate to be discharged. This dead volume is usually in the second hose section between the connecting point and the connector of the container.

Each volume of water transferred to the container is usually not adequate in order to dissolve a considerable part of the bicarbonate concentrate in the bag. Usually only 10–20% of the concentrate are dissolved in the bag. In a bag, for instance, having a capacity of 1.5 l and charged by approx. 650 g of sodium bicarbonate and approx. 1 l of water, approx. 100 g of sodium bicarbonate will be dissolved at ambient temperature, thus forming a saturated solution. Therefore a minimum of five more charging and discharging cycles may be performed without running the risk that a saturated concentrate will no longer be achieved.

In order to actually transform the water supplied by mixing with a powder concentrate to obtain a saturated solution, the solution in the bag is preferably agitated. This may be achieved by shaking the bag or subjecting it to ultrasonic waves in order to ensure a homogenous mixture.

On the other hand, however, the metering pump may be switched repeatedly to the charging and discharging phase with the second valve open and valves 1 and 3 permanently closed, therefore resulting in a pulsating charge and discharge of the concentrate bag.

The latter method, which is the preferred embodiment for compensating the dead volume, will also solve another problem, i.e. that of the dead volume, which occurs, as explained above, in the second hose section and its adjacent areas which are passed by both water and concentrate. Therefore residues, in particular of any water, have to be compensated for in this dead volume area. In so far it would be of advantage if valves 1–3 would be arranged as closely as possible to the connecting point. When the pump is repeatedly charged and discharged with the second valve open, the residual water in the dead volume will homogeneously mix with any previously saturated concentrate in the pump, followed by mixing in the bag. Therefore no diluted concentrate volumes will exist within the dead volume area.

On the other hand, however, it would be sufficient, in accordance with a specially preferred embodiment, if after the last discharge stroke of the metering pump another charging stroke of the pump would be performed whilst the second valve is still open during the water charging phase, therefore removing all the water from the dead volume area to the pump and, moreover, preferably a small quantity of saturated concentrate solution into the pump.

In all cases this is followed by stopping the pump, with saturated hemodialysis solution concentrate being provided there by the second and third valves which are open, followed by further mixing in the device for the production of a complete hemodialysis solution including any other electrolyte components.

On the other hand, for instance, the volume of the liquid concentrate solution conveyed including the dead volume may be determined by means of a flow sensor, regarding its ion components (sodium ions and bicarbonate ions), allowing compensation by control of the concentrate/water volume supplied.

This arrangement constitutes another preferred embodiment of a means for compensation for the dead volume. In this case concentration of the supplied water/concentrate mixture is continuously measured, and the device for the production of a ready-to-use hemodialysis solution is suitably controlled. On the other hand, of course, a predetermined liquid concentrate volume may also be supplied to the device for the production of a hemodialysis solution, not recognising and/or accepting this liquid concentrate volume as a concentrate but as added water. Such a mode of operation may be used in cyclic volumetric devices for the production of a hemodialysis solution, for instance as realised in the applicant's 2008 dialyser. In this dialyser, a hemodialysis solution is volumetrically produced by mixing predetermined parts of concentrate with water. For instance, one part of concentrate is put into a container, followed by adding 34 parts of water. According to the invention, the liquid volume initially supplied from the dead volume is considered as water, i.e. any pump strokes by which this liquid volume is supplied, are not considered to be concentrate strokes.

Furthermore, it is feasible to include an outlet instead of a metering pump through which this dead volume is passed to waste. For this purpose it is of advantage to provide a discharge pump which is briefly operated after charging the bag, with the second valve open. Such an arrangement is of advantage when pressurised RO water can be supplied to the flexible container. This pump may naturally be replaced by a fourth valve when the container can also be discharged under pressure. In such a case, the fourth valve will be opened until the water has been safely removed from the dead volume area and saturated concentrate is emerging from the outlet.

In principle one should note that the dead volume is approx. 1–2% of the supplied liquid volume, with losses being practically negligible.

Clamps may be used instead of valves if hoses are flexible. Furthermore, peristaltic pumps may replace these valves for stopping the hose system whilst de-activated.

The flexible container, preferably a bag, used for storing the dry concentrate, will be pressurised by water from the bottom as in the first embodiment, i.e. with the bag suspended, the connector is at its bottom. In order to avoid migration of dried concentrate after mixing with water, it is of advantage to use separating devices in the container. For instance, the connecting port of the container is closed by a semi-permeable diaphragm which is permeable to water and liquid concentrate but not to dry concentrate because of its particle size (approx. 0.3 mm and above). When water is added to this embodiment, dry concentrate is homogeneously mixed with water starting from the bottom, forming immediately a saturated concentrate when flowing through the powder to charge the container.

According to another embodiment, the container may be used in reverse, i.e. with the connector being at the top whilst in use. In such a case, a rising hose will be integrated in the bag, reaching down to the lowest point of the container. The end of the rising hose is in turn blocked by a semi-permeable diaphragm or a check valve allowing liquid concentrate to flow in but not to flow out. In the latter case a second port is arranged, close to the connector, in the rising hose, blocked by a second check valve in a direction opposite to the first check valve, allowing discharge only.

The shape and arrangement of the concentrate container may be freely selected as long as sufficient contact between the water and the dry concentrate is guaranteed during the charging phase.

BRIEF DESCRIPTION OF THE DRAWINGS

In the following.

Figure 1:
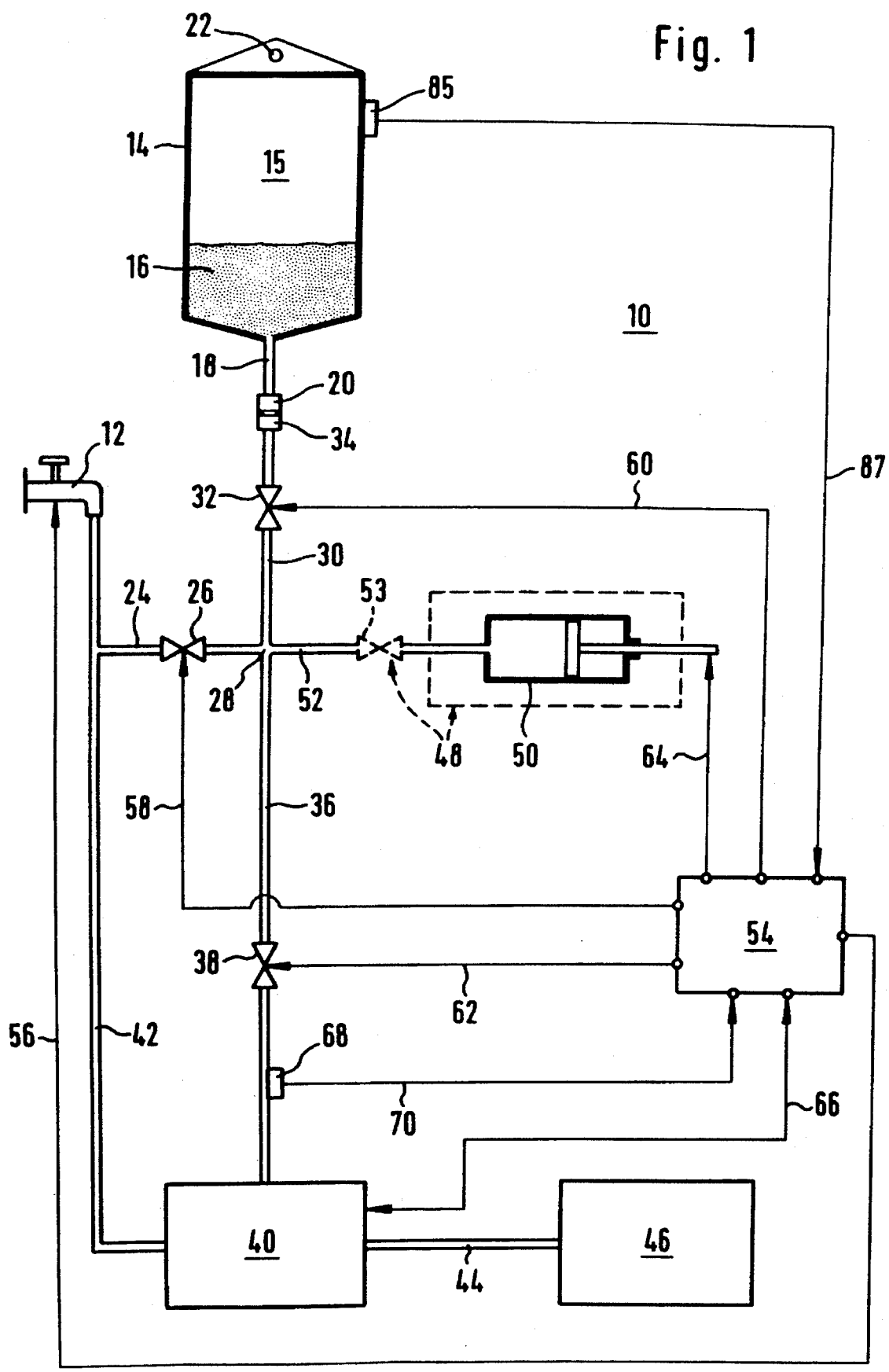
FIG. 1 is a diagram of a device for the production of a fluid concentrate.

Item 10 of FIG. 1 shows a device for the production of a liquid concentrate for hemodialysis. This device 10 includes a water supply 12, usually a stationary RO device. This water supply allows the continuous supply of pressurised or unpressurised water, which is essentially non-electrolytic. On the other hand, however, the water supply may consist of a water tank filled with a volume of water sufficient for continuously replenishing a container 14.

The container 14 is a flexible design, preferably a bag. For this purpose plastic foil is normally employed in the manufacture of such bags.

The container 14 is partially charged with a dry concentrate 16, normally having a particle size of 0.3 mm and above. Any electrolytes for hemodialysis may be used as a dry concentrate, preferably sodium bicarbonate, which is not very water-soluble. This dry concentrate is available in the bag in such a quantity that at least one hemodialysis treatment can be performed.

Should sodium bicarbonate be supplied in the container 14, all other concentrates (sodium chloride, potassium chloride, calcium chloride) should preferably be provided in another container, not shown, as dry or liquid concentrates.

The container normally contains approx. 500–1000 g of sodium bicarbonate (depending on the total liquid concentrate volume to be produced). Furthermore, the capacity of the container 14 is 2–4 times that of the initial volume of the powdered sodium bicarbonate and/or any other dry concentrates.

The container 14 includes a single tubular connector 18, with its end preferably having a first connecting piece 20.

Furthermore, the embodiment shown in FIG. 1 includes a suspension device 22 on the opposite side of the container 14, usually a loop, by which the container 14 can be suspended from a tripod not shown.

A first hose section 24 including a first valve 26, designed as a shut-off valve, is connected between the water supply and a connecting point 28. From there a second hose section 30 including a second valve 32 is arranged with a second connection 34 at its end leading to the connector 18. When used, the second connecting piece is connected to the first connecting piece 20, thus creating a flow connection between the second hose section 30 and the container 14 through the tubular connector 18.

Finally, a third hose section 36 is provided from connecting point 28, connected to a third valve 38. This third hose section 36 is connected to a device for the production of a hemodialysis solution 40.

This device 40 has only been sketched, with other concentrate supplies, if used, not being shown. Another water supply 42, connected to the water supply 12 only is shown, which is directly connected to the device 40. There the liquid concentrate supplied by hoses 30 and 36 is mixed with water in a predetermined ratio. This is followed by a ready-made liquid being supplied to the dialyser 46 by a hemodialysis solution hose 44.

Furthermore, a device for elimination of dead volume 48 is provided, as shown in dotted lines.

According to a preferred embodiment, this device for elimination of the dead volume 48 includes a metering pump 50 connected to the connecting point 28 by a fourth hose section 52. The metering pump 50 should preferably be a piston pump having a specific capacity and/or displacement.

According to another embodiment, the metering pump 50, which is initially used as a device for eliminating the dead volume, may also merely be used as a pump to convey fresh water.

Finally, a controller 54 is provided, connected through control lines 56, 58, 60, 62, 64 and 66 to the water supply 12, the first, second and/or third valves 26, 32, 38 of a device for elimination of the dead volume 48 and a device for producing a hemodialysis solution 40. Furthermore, a sensor 68 is arranged in the third line section 36, connected to the controller by a signal line 70. This controller 56 is available to measure the concentration of salt dissolved in the liquid concentrate, at least its quality, preferably, however, also its quantity by measuring the actual electrolyte concentration and flow through the hose section 36.

The embodiment shown in FIG. 1 of a device for the production of a liquid concentrate 10 will operate as follows:

During the charging phase, fresh water is passed from the water supply 12 through the first hose section 24, with the first valve activated, to the connecting point 28. Preferably the water supply 12 will supply pressurised RO water, for instance with a pressure of approx. 0.3 bar, which is passed through the second hose section 30, with the second valve 32 activated, and the tubular connector 18 to the bag 14 through the dry concentrate layer within the bag. The water volume supplied is finally determined by the capacity of the bag 14. This volume may be time-controlled (by the opening times of valves 26 and 32) when the water volume per time unit is known. On the other hand, a pressure of 0.2–0.3 bar will not be sufficient in order to burst the bag 14. Therefore a mere time control of valves 26 and 32 appears to be adequate.

When the water supply 12 is not pressurised, water will have to be passed by a pump arranged within the water supply 12, not shown, to the first hose section 24.

On the other hand, however, the volumetric pump 50 may be used as a conveying pump. In this case the two valves 26 and 32 are activated in opposite directions, i.e. valve 26 is open during the charging phase of pump 50, with the second valve 32 opening when discharging the pump, therefore conveying all the water previously passed to the pump 50 through the bag 14.

In this case the capacity of the pump 50 has been designed in such a way that the bag 14 may be charged by a maximum of 20–30 pump strokes. On the other hand, displacement of the pump 50 is at least double that of the dead volume of hose system 24, 30, 18, 36 described hereafter.

The powder concentrate 16 will flow from the tubular connector 18 in such a way that the liquid concentrate is saturated after the powder has passed the remaining cavity 15 of the container 14. This saturation process can furthermore be supported by discharging the liquid concentrate after the first valve 26 has been closed and instead the second valve 32 and the third valve 38 have been opened, therefore passing again through the solid concentrate layer 16. In this case, the liquid concentrate will flow through the connector 18 during the discharge phase, the second hose section 30 and the third hose section 36 to the device for the production of a hemodialysis solution 40 which usually consists of an inlet device, being a volumetric pump, not shown. In this stage of discharge of the container 14, the device 40 will receive a suitable activating signal from the controller 54 through the control line 66.

In order to maintain saturation of the concentrate solution, the dead volume within the hose system must be eliminated. This dead volume consists of hose sections through which both water and liquid concentrate are flowing, i.e. predominantly through the second hose section 30 and areas around the connecting point 28 including hose sections 24, 36 and possibly 52.

According to the first embodiment, the device for elimination of the dead volume 58 is designed as a pump 50, discharging the dead volume through the fourth hose section 52 whilst the valve 32 is open. At the end of this evacuation phase, saturated liquid concentrate will be available at connecting point 28 for further processing. The pump 50, having an adequate capacity, will be able to store the dead volume within the pumps 50. When the bag 14 is reversed to the charging phase, the pump 50 will receive a command from the controller 54 to discharge, i.e. to transfer the accumulated liquid volume to the bag 14.

In this embodiment, the pump 50 serves as a means for eliminating the dead volume from the neutral common hose section 30, with the liquid volume being accummulated within the pump 50.

Naturally, the pump 50 is also available to discharge the volume directly into an outlet if such an outlet is available. Similarly, a valve 53, as shown in dotted lines, may be installed in hose section 52 instead of the pump 50, provided that liquid concentrate is discharged under pressure from the bag 14, for instance by gravity, from the bag shown in FIG. 1, whilst valve 32 is open. In such a case and whilst valve 32 and discharge valve 53 are open, any liquid in the dead volume area may be conveyed to the outlet over a predetermined period of time.

Should the pump 50—as stated above—also be used for charging the bag 14, the dead volume is ejected during the first pump stroke, followed by allowing fresh water in whilst valve 26 is open.

According to another embodiment of the device for elimination of the dead volume 48, the pump 50 is used as a device for complete homogenisation of the contents of the bag 14 including any water in the dead volume. For this purpose the pump 50 is charged and discharged repeatedly with valve 26 closed and valve 32 open. The consequence is that both the dead volume and ready-to-use liquid concentrate is passed to the pump 50 and homogenised there, followed by this mixture being discharged into the bag 14 where it is concentrated again. After completion of several of such mixing operations, saturated liquid concentrate will fill the entire hose system 18, 30, 52, 36 and the pump 50.

Now concentration may be terminated, with pump 50 being deactivated and valve 38 being opened.

According to another embodiment, the device 40 for the production of a hemodialysis solution may receive a command from the controller 54, whilst the valve 38 is open, in order to pass a certain proportion of the liquid to be conveyed through hoses 30 and 36 as water and not as a liquid concentrate to the mixing chamber within the unit 40. For this purpose the hose section 36 will preferably be evacuated of any remaining liquid concentrate by operating valves 26 and 38, with the entire supply section for the liquid concentrate initially being filled with water. Owing to the feed rates of the pump provided in the device 40 and the dead volume usually being known, arrival of the concentrate in the unit 40 may be predetermined.

Furthermore, however, this arriving concentrate may be detected by means of a sensor unit 68, enabling a suitable signal to be activated via lines 70 and 66, enabling the unit 40 by a suitable signal through lines 70 and 66. Should the unit 40 be a proportional mixer, the proportional mixer may be set in such a way that the required composition of the hemodialysis solution is obtained when the dead volume and/or feed rate from the container 40 is known. In this case, the dead volume is initially regarded as water, with appropriately less water being fed through the water hose (based on a mixing ratio of concentrate and water of 1:34 and/or 1:16). At the mixing point, a calculated desired concentrate supply will be obtained in order to achieve the predetermined composition of the hemodialysis solution.

The end of the discharge phase of the bag 14 may be determined in several different ways. When the volumetric mixing system is used in the device 40 for the production of a hemodialysis solution, discharge can be accurately determined based on the known charging volume of the bag 14 due to the volumes withdrawn by the device 40. Therefore a suitable signal will be transmitted by line 66 to the controller 54 of the device 40 after reaching a predetermined volume.

The same may be found in proportional mixing systems in the device 40, the pumping rate of which is known for conveying liquid concentrate to a mixing point provided in the unit 40. Here, too, any liquid concentrate volume withdrawn may be determined by mere time control, with the controller 54 also being enabled by the unit 40 after expiry of that period of time.

Another embodiment to determine the end of the discharge phase consists of the controller 54 including a time segment, terminating the discharge phase after expiry of a certain period of time and again initiating the charging phase. This is useful when liquid concentrate volumes fed per time unit and water volumes conveyed to the bag 14 during the charging phase are known.

On the other hand, however, the degree of charging may be directly determined by a sensor 85 connected to the controller 54 through a signal line 87. This sensor 85 may be a length sensor arranged on the bag 14 by which the degree of expansion of the bag, both during charging and discharging, can be measured. In so far, such a length sensor may determine both the charging cycle and the discharging cycle in a predetermined way.

On the other hand, however, this sensor 85 may also gravimetrically determine the weight of the container 14, with preferably predetermined liquid volumes being measured by measuring the weight during supply and discharge.

At the end of the discharge phase, the third valve 38 will be closed, with the second valve 32 remaining open. At the same time the water supply 12, if not previously activated, and the first valve 26 will be activated, with fresh water again flowing to the bag 14 and being able to fill the same during the charging phase.

The end of the charging phase may, as stated above, be measured by the sensor 85, with the controller 54 closing at least the first valve 26 and initiating a discharge cycle. On the other hand, however, a mere time control is feasible when there is a guarantee that water from the water supply 12 will not burst the bag 14 after complete charging. This is guaranteed when the pressure under which water is supplied by the water supply 12 is below bursting pressure of the bag 14, usually below 0.2–0.3 bar.

Finally, a mere time control of the charging cycle is feasible, if the water volume and the charging volume of the bag 14 supplied per time unit are known. In such a control system, the first valve 26 will be kept open for a predetermined period of time, followed by closing. The charging phase will then be followed by a phase for eliminating the dead volume, with the discharging phase commencing after its completion.

Figure 2:
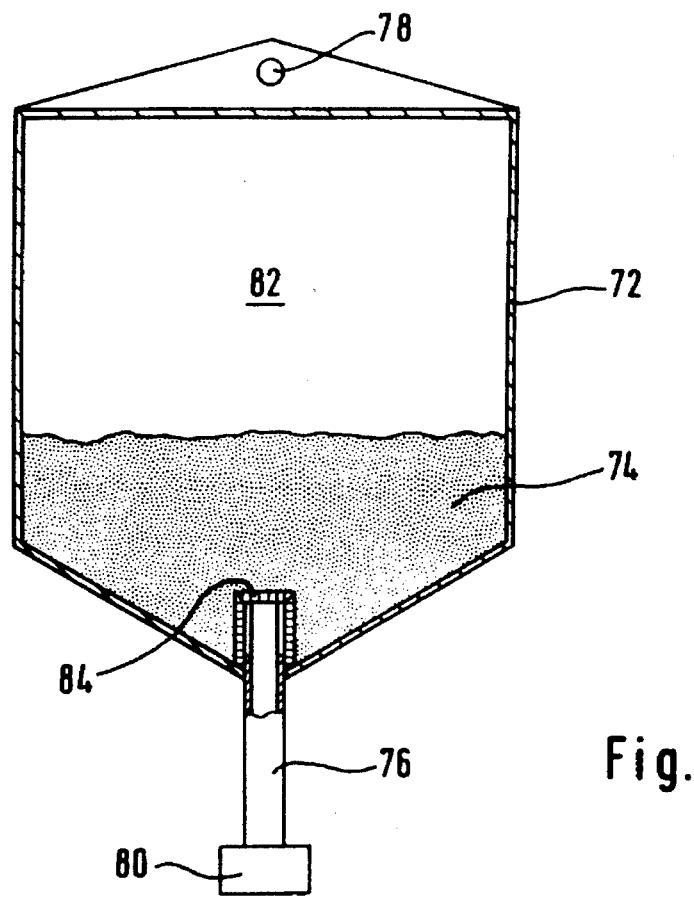
FIG. 2 is a diagram of the first embodiment of a dry concentrate bag.

FIG. 2 shows a first embodiment of the container 14 of the invention, as shown in FIG. 1, being designed as a bag 72, charged with a dry electrolyte concentrate, preferably sodium bicarbonate, of a volume sufficient for treatment of one patient during one session. Usually this quantity is between 500 and 800 g of bicarbonate, preferably having an average grain size of 0.5 mm and above. This layer of concentrate is referred to as 74.

The bag 72 shown in FIG. 2 is a suspended system, with a tubular connecting hose 76 being arranged at the bottom when in use. In contrast to the connecting hose 76, the edge of the bag 72 is provided with a loop for suspension.

Furthermore, the connecting hose 76 includes a connector 80, as stated above. There is a flow connection through the connecting hose 76 to the cavity 82 of the bag which is usually filled with concentrate to ⅓–¼ of its volume. The rest of the cavity 82 may be filled with water and/or saturated concentrate solution.

The end of the connecting hose 76 within the cavity 82 includes a semi-permeable diaphragm layer or filter layer 84, allowing inflowing water and outflowing concentrate solution to pass through but preventing concentrate powder or granules from flowing out through the connecting hose 76. A filter, for instance, will retain any particles having a grain size of more than 0.3 um. Contrary to this, smaller particles may be carried out by the concentrate flow, dissolving in the device 40 at the latest. Their concentration is so low that these would not effect significant changes in the composition of the hemodialysis solution.

Figure 3:
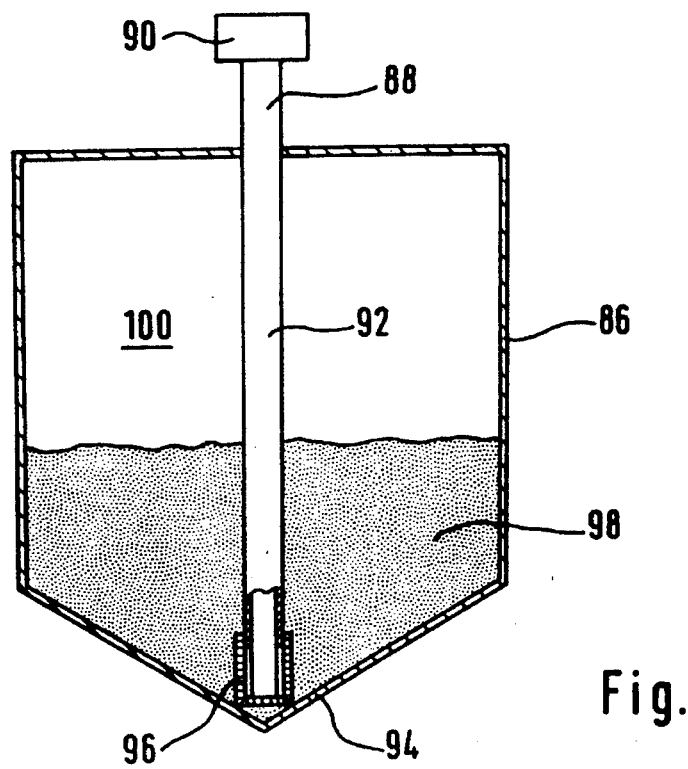
FIG. 3 is a diagram of a second embodiment of a dry concentrate bag.

FIG. 3 shows a design more or less similar to the embodiment of FIG. 2, but including a bag 86 in which the connecting hose 88 is at the top whilst in use. In this case, the connector 90 cannot only be used for connecting, but also for fixing the bag 86 to the dialyser, not shown.

The bag 86 includes a submerged pipe 92 extending into the connection from the connecting hose 88 to the bottom area 94, preferably being tapered and pointed towards the bottom, as shown in the embodiment of FIG. 3.

The end of the submerged pipe 92 is sealed with the same diaphragm or filter layer 96, as shown for 84 in the embodiment of FIG. 2.

This filter layer 96 is in the powder concentrate layer 98, which is similar to the concentrate layer 74.

The embodiments of FIGS. 2 and 3 offer the advantage that any liquid passed into the bags 72 and 86 will have to pass the concentrate layers 74 and 98 twice. The water, for instance, initially passes the concentrate layer when supplied, thus more or less and/or completely saturating with sodium bicarbonate. When the solution is later pumped from the cavity 82 and/or 100 of the bag 86, the solution flowing from the interior will have to pass the concentrate layer once again and will dissolve the concentrated powdered salt to saturation point unless previously saturated.

Figure 4:
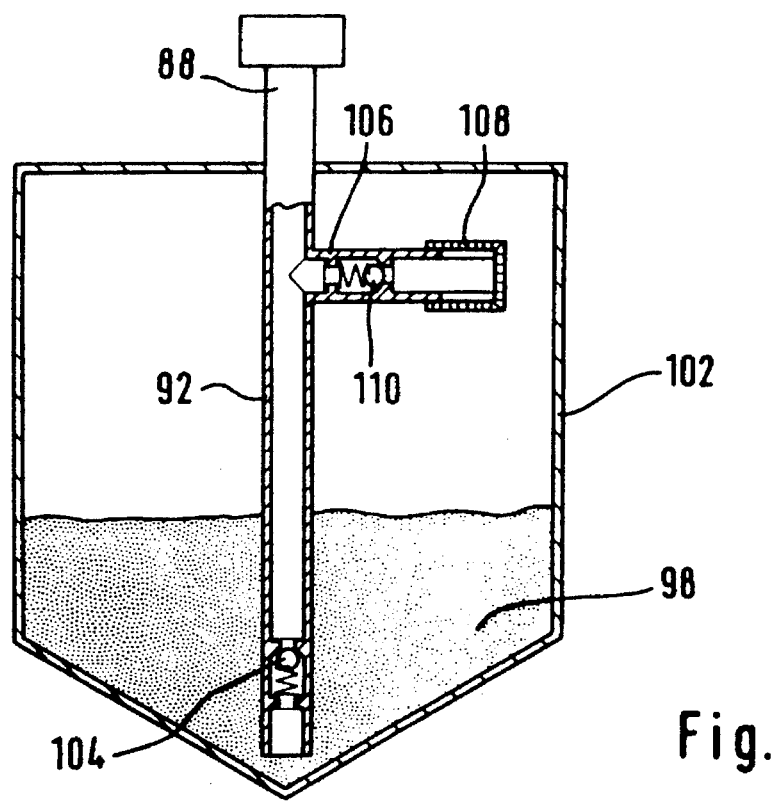
FIG. 4 is a diagram of a third embodiment of a dry concentrate bag.

FIG. 4 shows a third embodiment of a bag 102, essentially corresponding to the embodiment of FIG. 3. Therefore reference will be made to FIG. 3 and its reference numbers. In the embodiment shown in FIG. 4, however, only a flow of water through the submerged pipe 92 to its end is allowed in as the one-way valve 104 will block its return towards the connector 88. Consequently a discharge connection and/or a port 106 is provided in the submerged hose 92 in the vicinity of the connector 88 in the cavity 100 by which liquid concentrate can be discharged. According to a first embodiment, the end of the discharge hose 106 is sealed by a diaphragm and/or filter layer 108 corresponding to the filter layers 84 and 96 stated above. According to another embodiment, the discharge hose includes a second check valve 110 only allowing discharge in the direction of the discharge hose 88 but blocking the inflow of water.

Figure 5:
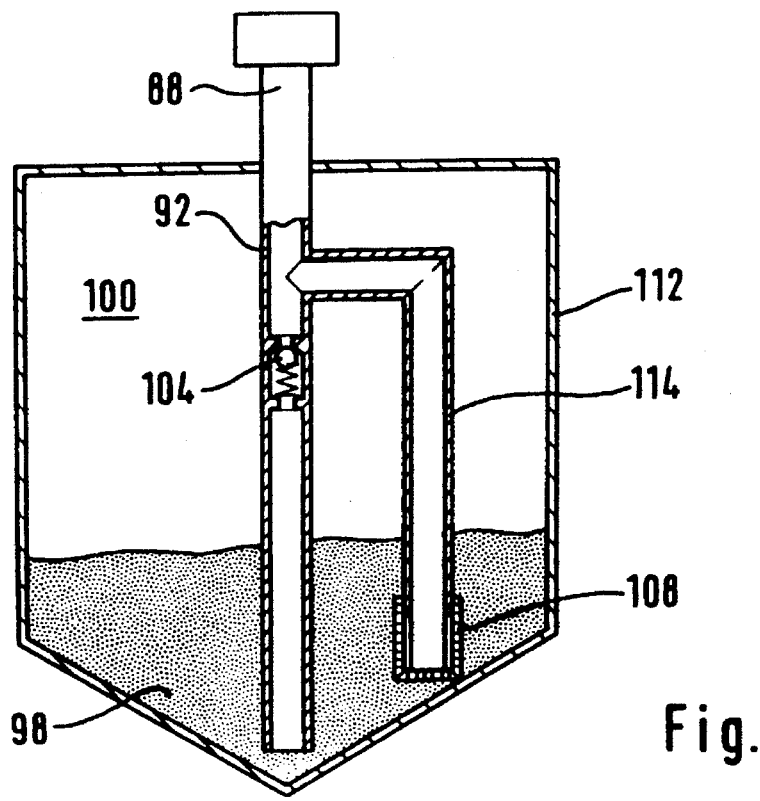
FIG. 5 is a diagram of a fourth embodiment of a dry concentrate bag.

Another embodiment of a bag 112 is shown in FIG. 5, mainly corresponding to the embodiment of FIGS. 4 and/or 3, with the same reference number being used for the same components.

A second submerged pipe 114 is provided instead of the discharge hose 106, sealed by a diaphragm 108. This submerged pipe passes through the concentrate layer 98 and is again sealed at its end by a filter layer 108. On the other hand, it is branching off next to the connecting pipe 88 within the bag 112 from the check valve 104 in the first submerged pipe 92.

In this case, the first check valve 104 allows the inflow of water through the cavity 100 and the concentrate layer 98, but blocking the return. This return flow passes through the filter layer 108, the second submerged pipe 114, the top section of the first submerged pipe 92 and the connecting hose 88.

Each of the bags, 72, 86, 102 and 112 is a separate commercial unit and may be connected to the device 10 if required. The term "bag" does not only include standard plastic bags, preferably made of a clear, translucent material, but also solid-wall containers including a vent, usually a hydrophobic diaphragm, allowing the passage of air but not water. Such a container may also consist of clear plastic material or even glass. Such solid-wall containers may be useful when concentrates are dissolved in which no gas is generated, such as by metering of bicarbonate in carbonate and $CO_2$. In this case, a solid-wall container is not preferred for the dissolution of bicarbonate.

I claim:

1. A flexible medical packaging unit for hemodialysis for the production of a hemodialysis solution concentrate, comprising a flexible container providing a single connector and a cavity charged with a powdered salt concentrate of a quantity sufficient for one hemodialysis treatment, and wherein the volume of the cavity of the container is so designed that the powdered salt concentrate is only partially dissolved when completely charged with water.

2. A packaging unit according to claim 1, in which the salt concentrate is sodium bicarbonate.

3. A packaging unit in accordance with claim 1 in which the flexible container is a plastic bag.

4. A packaging unit according to claim 1 comprising a filter layer adjacent to the connector in the cavity of the container, creating a flow connection from the connector to the cavity.

5. A packaging unit according to claim 1 in which said container comprising a floor area on which the concentrate is disposed, a top spaced from said concentrate, and a submerged pipe extending from the connector through the cavity of the container from the top to the floor area.

6. A packaging unit according to claim 5, in which the end of the submerged pipe in the floor area is sealed by a filter layer.

7. A packaging unit according to claim 5, comprising a first check valve within the submerged pipe, allowing flow in the direction of the floor area of the container only, the submerged pipe adjacent to the connector including a port, a second check valve being provided at the port having a port filter layer for releasing a flow of liquid only in the direction of either the connector or the port filter layer.

8. A packaging unit in accordance with claim 7, wherein the discharge hose extends to the concentrate.

9. A system for the production and discharge of a liquid hemodialysis concentrate comprising a water supply, a flexible container having a single connector and connecting hose, including a sufficient quantity of a concentrate powdered salt, connecting on the one hand the water supply and on the other the connector and a device for the production of a hemodialysis solution, shut-off systems each opening and/or closing the hose system in a predetermined way, a controller for activating said water supply, a shut-off system and the hemodialysis solution producing device, and a device for compensating dead volume formed by at least one hose passed by both water and liquid concentrate, said controller enabling said dead volume compensating device prior to commencement of discharge of the liquid concentrate.

10. A system according to claim 9, comprising a first hose section including a connecting point and a first valve, a second hose section including a second valve between the connecting point and the connecting hose, a third section including a third valve between the connecting point and the hemodialysis solution producing device, and a fourth hose section connected to the connecting point, connected in circuit with the dead volume compensating device to eliminate the dead volume.

11. A system according to claim 10, in which the dead volume compensating device is a metering pump activated by the controller.

12. A system according to claim 11, wherein said metering pump is operated during elimination of the dead volume by the controller, with the second valve open and other valves closed, ensuring that at least full dead volume in said hoses will be evacuated, and accumulated within said metering pump.

13. A system according to claim 11, wherein the metering pump is controlled by the controller to charge and discharge during the elimination of the dead volume, with the second valve open and other valves closed.

14. A system according to claim 10, in which the dead volume compensating device comprises a fourth valve and a fourth hose section from said valve to said connecting point said fourth valve being opened together with the second valve by the controller for such a period of time that the dead volume is eliminated by the fourth hose section.

15. A system according to claim 9, wherein the device for elimination of the dead volume controls the device for production of the hemodialysis solution in such a way that liquid in the dead volume will be conveyed for the production of hemodialysis solution.

16. A system according to claim 15, including a sensor for continuously determining the composition of any liquid passing through the third hose section and signaling to the controller (54) when a predetermined reading is reached for the composition and/or volume of liquid, whereby the device for the production of hemodialysis solution is switched to convey the liquid concentrate.

17. A system according to claim 9, in which the controller deactivates the device for the production of hemodialysis solution at the end of its discharge, closing the third valve and activating the water supply as well as the first and second valves in a predetermined way in order to initiate charging.

* * * * *